US005368587A

United States Patent [19]

Lechleiter

[11] Patent Number: 5,368,587

[45] Date of Patent: Nov. 29, 1994

[54] AMPULE SHIELD

[75] Inventor: Robert J. Lechleiter, West Orange, N.J.

[73] Assignee: Akzo Nobel N.V., Arnhem, Netherlands

[21] Appl. No.: 61,032

[22] Filed: May 14, 1993

[51] Int. Cl.[5] .............................................. A61B 19/00
[52] U.S. Cl. ...................................... 604/416; 206/219
[58] Field of Search ......................... 366/602; 206/219; 604/310, 311, 411, 416, 192

[56] References Cited

U.S. PATENT DOCUMENTS 5,084,032 1/1992 Kornberg et al. .................. 604/192

*Primary Examiner*—Jerome L. Kruter
*Attorney, Agent, or Firm*—Spencer, Frank & Schneider

[57] ABSTRACT

An ampule shield has a center tube with an upper end, and an outer tube extending coaxially with the center tube and attached to the center tube below the upper end of the center tube. The outer tube extends some distance beyond a lower end of the center tube. The outer tube is spaced from the center tube to provide a cylindrical space within the shield for receiving an ampule. A removable cap for attachment to a bottom of the outer tube is provided.

10 Claims, 2 Drawing Sheets

AMPULE SHIELD

BACKGROUND OF THE INVENTION

1. Field of the Invention

The present invention relates generally to the field of medical devices, and in particular to an ampule shield.

2. Background Information

Homan U.S. Pat. No. 4,645,073 discloses a package for enabling a user to mix a diluent with a hazardous material and then fill a syringe with the resultant solution without endangering the immediate environment which comprises an elastomerically stoppered glass vial containing the material and a sealed transparent plastic bag enclosing the vial and having a septum means therein to sealingly receive the needle of a diluent containing syringe therethrough as the needle moves through the stopper of the vial to provide a seal when the needle is withdrawn.

Fournier et al. U.S. Pat. No. 4,982,769 also discloses a package for enabling a user to mix a diluent with a hazardous material and then fill a syringe with the solution without endangering the immediate environment, but this package requires that the package container after opening interengage with the packaged device (having means for cooperating with a medicament vial for use therewith) to provide a sealed interior space in which means for cooperating with a vial is operable to cooperate with a vial contained in the space.

Kolber et al. U.S. Pat. No. 5,171,214 discloses a system for separately storing and subsequently mixing the contents of at least two containers in one of the containers which comprises two containers, a syringe assembly attached to the second container and extending between the two containers, and an adapter connecting the first container or vial to the syringe assembly wherein a skirt member circumscribes the outside of the vial and has rachet means that cooperates with complementary rachet means on the adapter to prevent disengagement of the vial from the adapter.

SUMMARY OF THE INVENTION

The present invention was therefore developed to provide an efficient ampule shield. The present invention provides the following novel features and advantages.

It should be remembered that the present invention was developed to help facilitate the reconstitution of a freeze dried medicinal preparation packaged within a glass ampule. The device, therefore, provides a "closed" system which minimizes or eliminates any exposure of the contained product to the clinician during mixing and draw-up into a syringe. However, the invention as defined in the claims may be readily adaptable to other applications, as would be apparent to one skilled in the art.

According to an embodiment of the invention, the ampule shield comprises a center tube having an upper end portion, an outer tube extending coaxially with and attached to the center tube some distance from the upper end portion of the center tube, and extending some distance beyond a lower end of the center tube, the outer tube being spaced from the center tube to provide a cylindrical space within the shield for receiving an ampule, and a removable cap for attachment to a bottom of the outer tube.

According to another embodiment, an interior wall of the outer tube is inwardly tapered at an upper end to fit an ampule when disposed in the shield. In another embodiment of the ampule shield, the cap includes a raised central portion for resting against an ampule bottom when disposed in the shield. In one embodiment, the raised portion is in the shape of a cross.

In another advantageous embodiment, a standard male luer fitting is provided at the upper end portion thereof.

In another embodiment, the outer tube is provided with an outwardly extending lip and the cap is provided with a corresponding recess for engaging the lip when the cap is assembled to the outer tube.

According to another embodiment, the ampule shield is used with an opened ampule containing a freeze-dried substance, the center tube extending into the ampule and into the freeze-dried substance, the outer tube encompassing an outer surface of the ampule, and the cap closing the ampule within the shield. A syringe containing a diluent attaches to the standard male lure fitting. An embodiment of a method of reconstituting a freeze-dried substance in an opened ampule comprises utilizing this embodiment of the ampule shield.

In another embodiment, an ampule shield for use with an opened ampule includes first tube means having an end for extending into an inside of an opened ampule, second tube means, concentric with and attached to the first tube means, for surrounding outside walls of an opened ampule, and cap means, attachable to the second tube means, for enclosing an opened ampule within the ampule shield.

According to another embodiment, the first tube means further includes engagement means, disposed at an end thereof opposite the end which extends into an opened ampule, for engaging an external device which can provide a diluent through the first tube means into an opened ampule.

These and other objects and aspects of the invention are better understood with reference to the detailed description and accompanying drawings, and it will be understood that changes in the specific structure shown and described may be made within the scope of the claims without departing from the spirit of the invention.

Figure 1B:
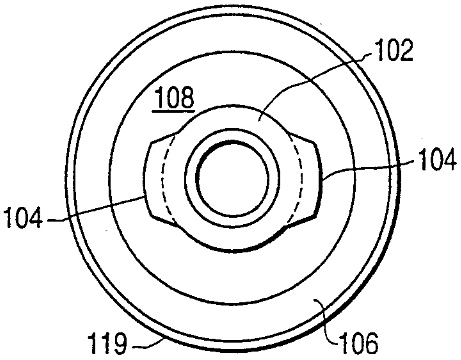
FIG. 1 is a longitudinal cross-sectional view of an embodiment of the invention.
Figure 1A:
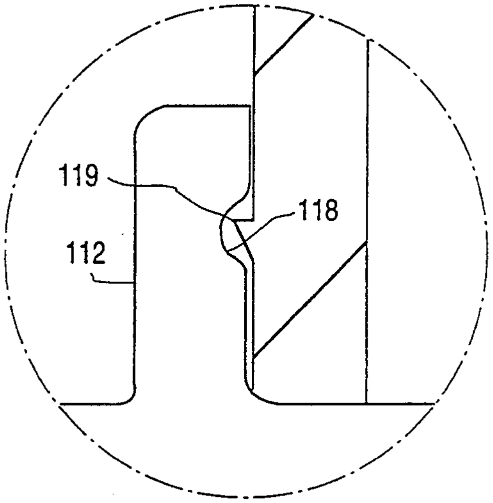
Figure 1:
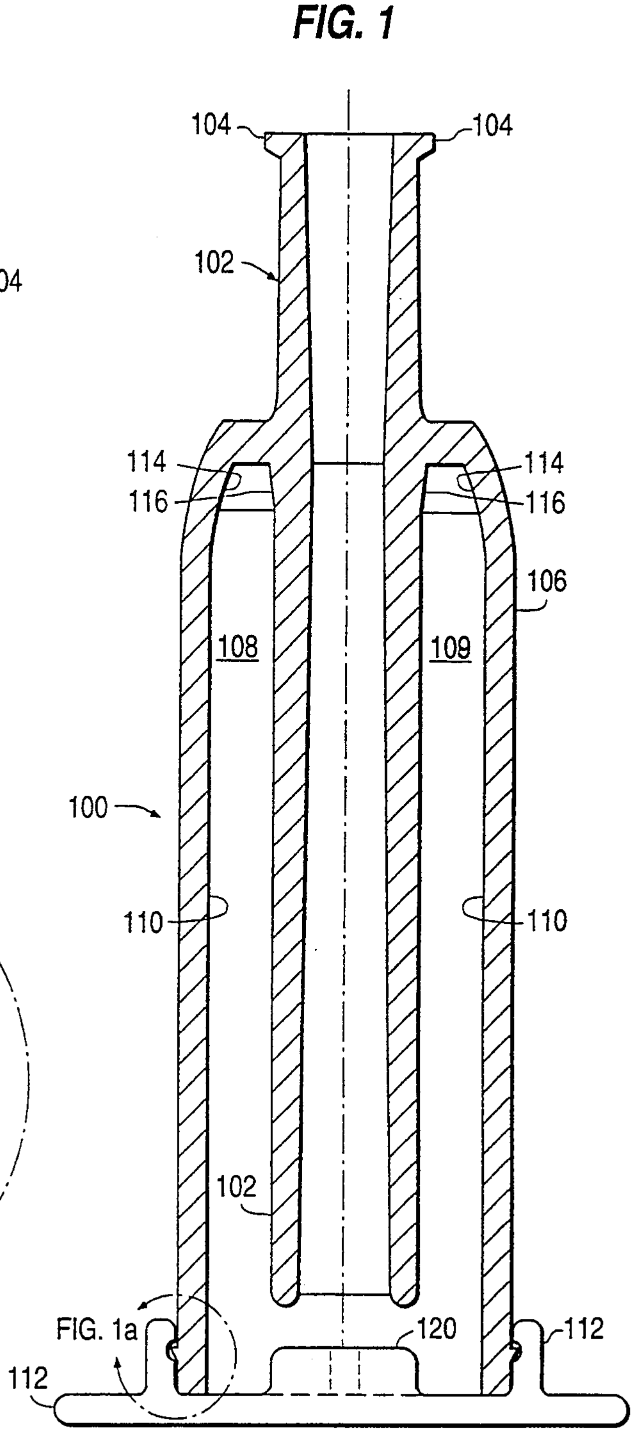
Figure 2:
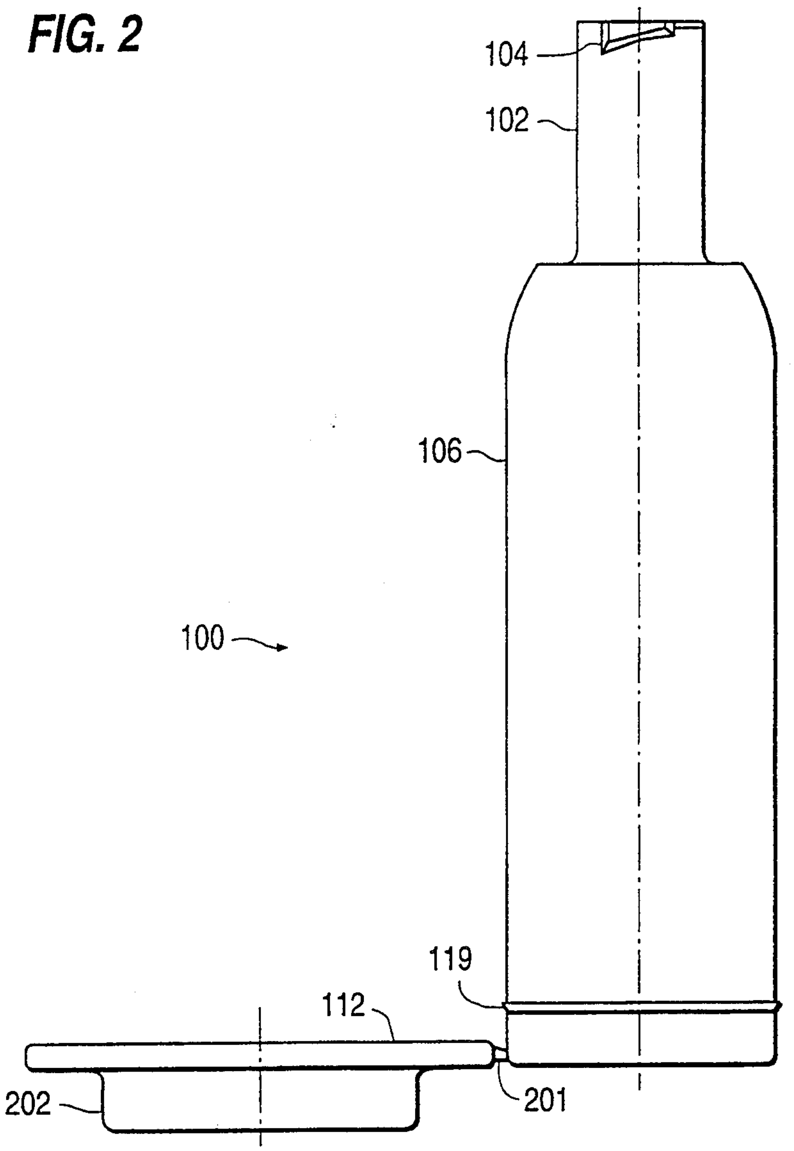

FIG. **1*a* is an enlargement of a portion of FIG. 1**;

FIG. **1*b* is an end view from the top of the embodiment according to FIG. 1**;

FIG. 2 is an outside longitudinal view of an embodiment shown with the cap attached to the body by a breakable nib; and FIG. **2*a* is a bottom end view of the embodiment of FIG. 2**.

DETAILED DESCRIPTION OF THE PREFERRED EMBODIMENTS

The invention will now be described in more detail by example with reference to the embodiments shown in the Figures. It should be kept in mind that the following described embodiments are only presented by way of example and should not be construed as limiting the inventive concept to any particular physical configuration.

With reference to the longitudinal cross-sectional view of FIG. 1, the ampule shield 100 comprises a center or inner tube 102 having a standard male luer fitting 104 at an upper end portion, a coaxial outer tube 106 attached to the center tube 102 near the upper end and extending a short distance beyond a lower end thereof.

The outer tube 106 is set off from the center tube 102 to provide a cylindrical space 108 within the shield 100. The interior wall 110 of the outer tube 106 has an inward taper 114 at the upper end. A removable cap 112 fits onto the bottom of the outer tube 106. In use, an ampule is secured in the shield 100 with the cap 112. The inward taper 114 on the outer tube 106 is intended to conform with an open end of an ampule in a friction fit. However, since not all ampules break cleanly, the taper 114 alone cannot be relied on to achieve a good seal.

An outward taper 116 at the upper end of the inner tube 102 may also be provided to better fit an ampule. In this embodiment, the inner tube 102 outward taper 116 frictionally engages with the inside of an ampule opening, while the outer tube 106 inward taper 114 simultaneously frictionally engages with the outside of the ampule opening.

As can be seen in the enlarged portion of FIG. 1*a*, the outer tube 106 is provided with a circumferential, outwardly extending lip 119 which engages a corresponding recess 118 in cap 112 to provide a secure seal therebetween. The illustrated cap 112 also has an upwardly projecting portion 120 on which the bottom of an ampule would rest when the cap 112 is assembled to the tube 106.

FIG. 1*b* shows an end view from the top of the shield 100. Male luer fitting 104 and circumferential lip 119 can be readily seen in this figure.

The ampule shield 100 could be used for any freeze-dried product dispensed in ampules, thus facilitating reconstitution of freeze-dried medicinal preparations normally packaged in glass ampules. In such a use, the tube portions 106 and 102 of the shield 100 would be slipped onto an open ampule containing a freeze-dried material (not shown) so that the lower end of the center tube 102 extends inside the ampule and penetrates the freeze-dried material and the interior inward taper 114 of outer tube 106 seals off the opening around the upper portion of the ampule. The cap 112 is then affixed to the bottom of the outer tune 106 of shield 100 effectively sealing the system.

The center tube 102 is designed to have a length which extends into the material in the bottom of the ampule but stops just short of bottoming out on the ampule. Sufficient space will thus exist to permit the flow of diluent from a syringe through the tube 102 to reconstitute a freeze-dried substance in the ampule and withdraw the reconstituted substance back up tube 102 into the syringe.

The diluent or a solvent would then be dispensed into the ampule through tube 102 by means of, for example, a syringe (not shown) attached to the LUER fitting 104 of the ampule shield 100 center tube 102 to reconstitute the freeze-dried material in the ampule. The reconstituted or mixed product would then be withdrawn completely into the syringe. Any leakage around the open end of the ampule which might occur is trapped inside the shield 100.

A standard female LUER cap (not shown) can thereafter be placed on the fitting 104 of tube 102 so that the complete unit, i.e., the shield 100 with ampule therein, can be sealed and discarded. This helps to prevent accidental exposure to any unused product remaining in the ampule.

In a preferred embodiment, the ampule shield 100 is injection molded of a clear, medicinal grade of thermoplastic. Its parts are preferably composed of a clear, good clarity thermoplastic such as medical grade polypropylene, polystyrene or "K-Resin" (butadiene-styrene copolymer).

The illustrated shield 100 was designed for a specific application, i.e., for use with Tice®-BCG product which is contained in a 2 mL. ampule. However, the invention is not limited to such use and could be produced to accommodate other ampule sizes, e.g., 1 mL., 5 mL., 10 mL., etc., and designs.

In this regard it is noted that there are several glass manufacturers supplying the market with ampules, such as Wheaton Glass, O-I Kimble, Comar Glass and others. Each company offers various "standard" sizes but from company to company the standards frequently differ in diameter or height dimensions. There is thus no apparent "industry" standard for ampules. Thus, the particular dimensions of an embodiment of the present invention would depend on the ampuie it is to be used with.

There is no pressure relief system featured in the illustrated design, however, such a modification would be well within the ability of one skilled in the art, and would be considered within the scope of the claims. A venting system is not necessary in applications where only a small amount of diluent, e.g., 1 to 2 mL., is required. Such a low volume of fluid does not introduce any significant pressure into the ampule shield 100, even when closed by cap 112. The seal between the cap 112 and the outer tube 106 and the seal between the ampule opening and the tapered upper portion is sufficient to prevent the ampule from being ejected from the shield under these conditions.

Figure 2A:
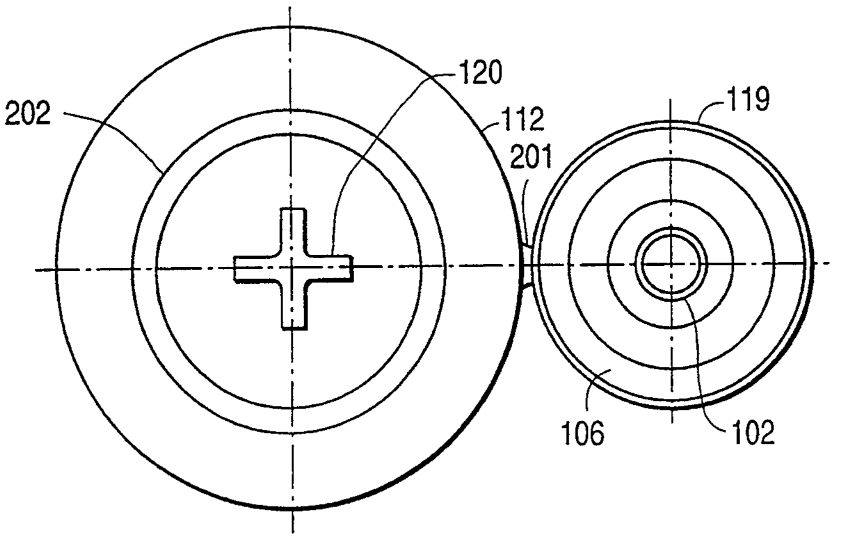

FIG. 2 shows a side view of the shield 100, which may be manufactured with a single mold, with breakable nib 201 connecting outer tube 106 and cap 112. Cap 112 can be seen to have a flat base portion and an extending portion 202 which fits around the outside of outer tube 106 when assembled thereto. As can be seen in FIG. 2*a*, a bottom end view of the shield 100, the raised portion 120 of the base 112, on which the bottom of an ampule will rest in use, is made in the form of a cross.

It is understood that various other modifications will be apparent to and can be readily made by those skilled in the art without departing from the scope and spirit of the present invention. Accordingly, it is not intended that the scope of the claims appended hereto be limited to the description set forth above but rather that the claims be construed as encompassing all of the features of patentable novelty which reside in the present invention, including all features which would be treated as equivalents thereof by those skilled in the art to which the invention pertains.

For example, pressure relief means could be provided for applications where a large amount of diluent will be added to an ampule within the shield. Such pressure relief means could take any number of forms, as would be readily apparent to one skilled in the art.

The interior contours of the shield may be varied in design to fit a particular type of ampule. The illustrated embodiment is of a generally circular-type cross-section, however, other cross-sections could be used within the scope of the invention to accommodate corresponding ampules so configured.

The preferred embodiment is formed of medical grade polypropylene, polystyrene or "K-Resin" (butadiene-styrene copolymer), however, other suitable materials well known to those skilled in the technology may be substituted therefore.

What is claimed:

1. An ampule shield comprising:

a center tube having an upper end portion;

an outer tube extending coaxially with and attached to the center tube some distance from the upper end portion of the center tube, and extending some distance beyond a lower end of the center tube, the outer tube being spaced from the center tube to provide a cylindrical space within the shield for receiving an ampule; and a removable cap for attachment to a bottom of the outer tube.

2. An ampule shield according to claim 1, wherein an interior wall of the outer tube is inwardly tapered at an upper end to fit an ampule when disposed in the shield.

3. An ampule shield according to claim 1, wherein the cap includes a raised central portion for resting against an ampule bottom when disposed in the shield.

4. An ampule shield according to claim 3, wherein the raised portion is in the shape of a cross.

5. An ampule shield according to claim 1, wherein a standard male luer fitting is provided at the upper end portion thereof.

6. An ampule shield according to claim 5, wherein the outer tube is provided with an outwardly extending lip and wherein the cap is provided with a corresponding recess for engaging the lip when the cap is assembled to the outer tube.

7. An ampule shield according to claim 6, used with an opened ampule containing a freeze-dried substance, wherein the center tube extends into the ampule and into the freeze-dried substance, the outer tube encompasses an outer surface of the ampule, and the cap closes the ampule within the shield, and wherein a syringe containing a diluent attaches to the standard male luer fitting.

8. A method of reconstituting a freeze-dried substance in an opened ampule which comprises utilizing the ampule shield of claim 7.

9. An ampule shield for use with an opened ampule, comprising:

first tube means having an end for extending into an inside of an opened ampule;

second tube means, concentric with and attached to the first tube means, for surrounding outside walls of an opened ampule; and cap means, attachable to the second tube means, for enclosing an opened ampule within the ampule shield.

10. An ampule shield according to claim 9, wherein the first tube means further includes engagement means, disposed at an end thereof opposite the end which extends into an opened ampule, for engaging an external device which can provide a diluent through the first tube means into an opened ampule.

* * * * *